(12) United States Patent
Wong (10) Patent No.: US 12,127,946 B2
(45) Date of Patent: Oct. 29, 2024

(54) LOW-PROFILE PROSTHESES, SYSTEMS, AND METHODS

(71) Applicant: Wright Medical Technology, Inc., Memphis, TN (US)

(72) Inventor: Kian-Ming Wong, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 22 days.

(21) Appl. No.: 17/653,053

(22) Filed: Mar. 1, 2022

(65) Prior Publication Data

US 2022/0313446 A1  Oct. 6, 2022

Related U.S. Application Data

(60) Provisional application No. 63/169,494, filed on Apr. 1, 2021.

(51) Int. Cl.
*A61F 2/42* (2006.01)
*A61F 2/30* (2006.01)

(52) U.S. Cl.
CPC ........ *A61F 2/4202* (2013.01); *A61F 2/30771* (2013.01); *A61F 2002/30878* (2013.01); *A61F 2220/0016* (2013.01)

(58) Field of Classification Search
CPC ................. A61F 2002/4205; A61F 2/4202
See application file for complete search history.

(56) References Cited

U.S. PATENT DOCUMENTS

| | | | | |
|---|---|---|---|---|
| 6,015,937 A | * | 1/2000 | Braanemark | A61F 2/4202 606/65 |
| 9,615,856 B2 | * | 4/2017 | Arnett | A61B 17/0642 |
| 2007/0055380 A1 | * | 3/2007 | Berelsman | A61F 2/4612 623/908 |
| 2011/0035019 A1 | | 2/2011 | Goswami et al. | |
| 2013/0123863 A1 | * | 5/2013 | Hollis | A61B 17/68 606/328 |
| 2014/0277530 A1 | * | 9/2014 | Stalcup | A61F 2/3859 623/20.14 |
| 2018/0042730 A1 | * | 2/2018 | Nachtrab | A61F 2/4202 |
| 2019/0070012 A1 | | 3/2019 | Leerijse et al. | |
| 2021/0038402 A1 | * | 2/2021 | Lee | A61F 2/42 |

(Continued)

FOREIGN PATENT DOCUMENTS

CN        107374788 A    11/2017

OTHER PUBLICATIONS

Definition of adjacent obtained from https://www.merriam-webster.com/dictionary/adjacent#:~:text=%C9%99%2D%CB%88j%C4%81s%2D%E1%B5%8Ant-,1,vertex%20and%20side%20in%20common on Nov. 3, 2023 (Year: 2023).*

(Continued)

*Primary Examiner* — Ariana Zimbouski
*Assistant Examiner* — Yasniary De La Caridad Morales
(74) *Attorney, Agent, or Firm* — DUANE MORRIS LLP (57) ABSTRACT

A system includes a first prosthesis. The first prosthesis may include a body extending along a length from a first side to a second and including a third side disposed between the first side and the second side. The body may include a pair of spaced apart rails between which a channel is defined. A stem and a first fixation element may extend upwardly from the third side. A method may include coupling the first prosthesis to bone.

17 Claims, 7 Drawing Sheets

(56) References Cited

U.S. PATENT DOCUMENTS

2021/0330473 A1\* 10/2021 Hunt .................... A61F 2/2803
2022/0202583 A1\* 6/2022 Axelson, Jr. .......... A61F 2/4081

OTHER PUBLICATIONS

Extended European Search Report issued in connection with corresponding European Patent Application No. 22160297.2, Aug. 8, 2022, 9 pages.

\* cited by examiner

LOW-PROFILE PROSTHESES, SYSTEMS, AND METHODS

CROSS-REFERENCE TO RELATED APPLICATION

This application claims priority to U.S. Provisional Patent Application No. 63/169,494, filed Apr. 1, 2021, the entirety of which is incorporated by reference herein.

FIELD

The disclosed apparatuses, systems, and methods relate to joint replacements. More particularly, the disclosed apparatuses, systems, and methods relate to ankle replacements with enhanced fixation.

BACKGROUND

The ankle is a joint that acts much like a hinge. The joint is formed by the union of three bones: the talus, tibia, and fibula. The talus (sometimes referred to as the "ankle bone") fits inside a socket that is formed by the lower end of the tibia and the fibula. Arthritis, bone degeneration, and/or injury can cause ankle joint deterioration resulting in pain, reduced range of motion, and decreased quality of life. In many cases, physicians are recommending ankle replacement surgery with an implant as an option. Providing ankle replacement systems that have good fixation to the distal tibia is desirable.

SUMMARY

In some embodiments, a prosthesis includes a body extending along a length from a first side to a second side and including a third side disposed between the first side and the second side. The body includes a pair of spaced apart rails between which a channel is defined. A stem and a first fixation element extend upwardly from the third side.

In some embodiments, a system includes a first prosthesis. The first prosthesis includes a body extending along a length from a first side to a second and including a third side disposed between the first side and the second side. The body includes a pair of spaced apart rails between which a channel is defined. A stem and a first fixation element extend upwardly from the third side.

In some embodiments, a method includes coupling a first prosthesis to a bone. The first prosthesis includes a body extending along a length from a first side to a second and including a third side disposed between the first side and the second side. The body includes a pair of spaced apart rails between which a channel is defined. A stem and a first fixation element extend upwardly from the third side.

DETAILED DESCRIPTION

This description of the exemplary embodiments is to be read in connection with the accompanying drawings, which are to be considered part of the entire written description.

This description is to be read in connection with the accompanying drawings, which are to be considered part of the entire written description. In the description, relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIGS. 1-8 illustrate one example of a prosthesis in accordance with some embodiments. In some embodiments, prosthesis 100 may be a tibial tray or platform, such as a tibial tray or platform described in U.S. Pat. No. 8,715,362 (the "'362 Patent") and/or U.S. Pat. No. 10,136,904 (the "'904 Patent"), the entireties of which are incorporated by reference herein. However, although prosthesis 100 is described as being a tibial prosthesis for an ankle replacement system, one of ordinary skill in the art will understand that the disclosure is not so limited and the prosthesis could be adapted for other joints and/or body parts.

Figure 1:
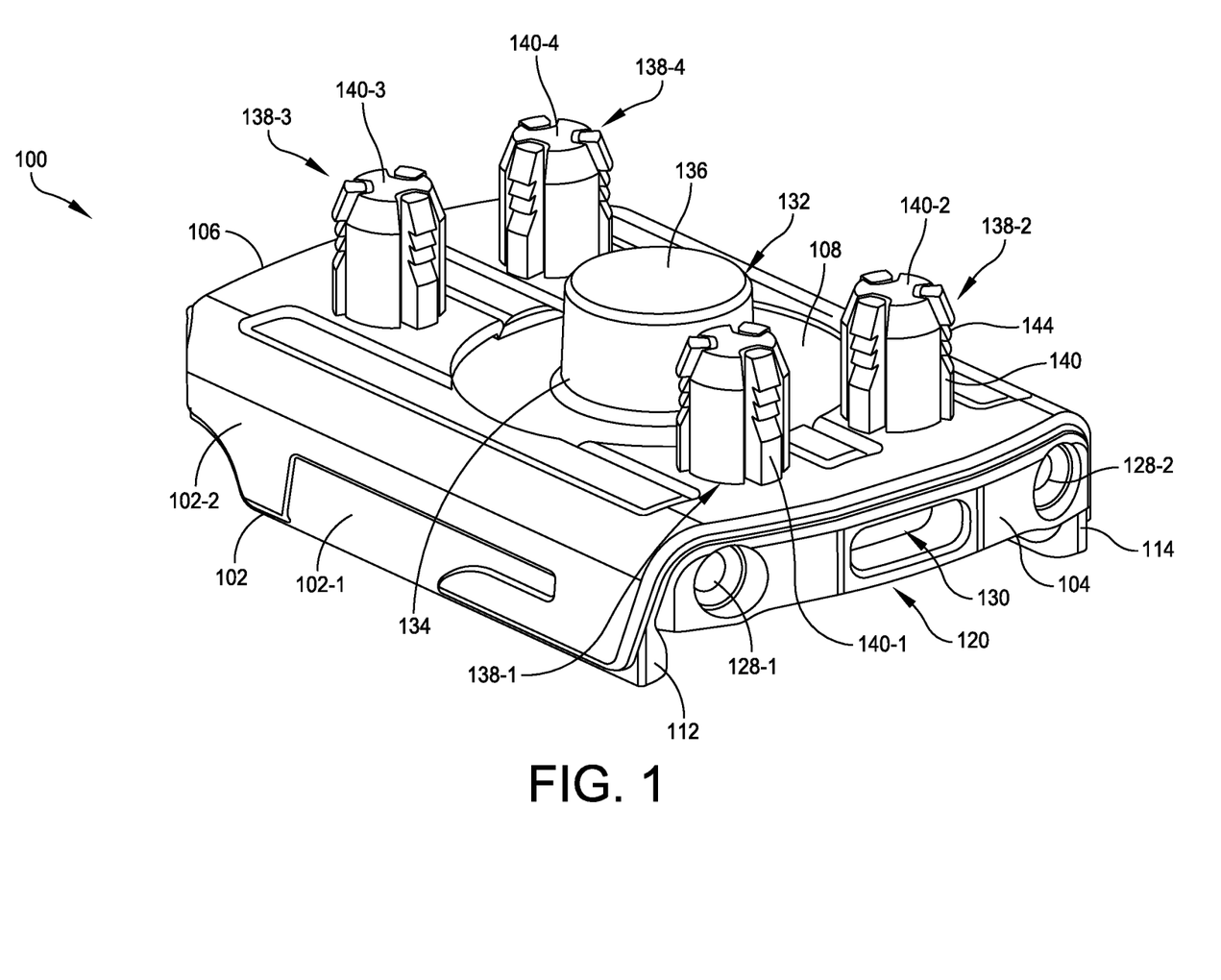
FIG. 1 is an isometric view of one example of a prosthesis in accordance with some embodiments.

Prosthesis 100 may include a body 102 extending in a longitudinal direction from a first side 104 to a second side 106. In some embodiments, first side 104 is a front side (e.g., a side facing an anterior bone surface) and second side 106 is a back or rear side (e.g., a side facing a posterior bone surface). Body 102 may also have a third side 108 that extends between the first side 104 and the second side 106. In some embodiments, side 108 is an upper side providing an upper surface 110.

Figure 4:
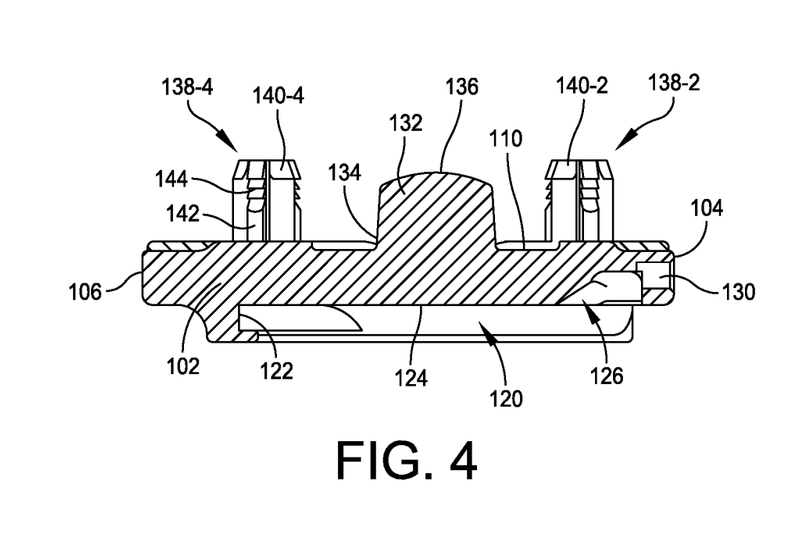
FIG. 4 is a cross-sectional view of the prosthesis illustrated in FIG. 1 taken along line 4-4 in FIG. 2 in accordance with some embodiments.
Figure 5:
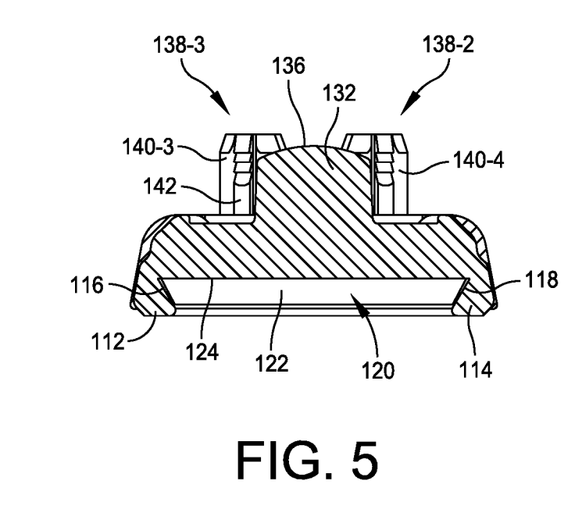
FIG. 5 is a cross-sectional view of the prosthesis illustrated in FIG. 1 taken along line 5-5 in FIG. 3 in accordance with some embodiments.

As best seen in FIGS. 1 and 5, body 102 may include a pair of spaced apart side rails 112, 114 that form the side walls 116, 118 of a channel 120 that extends inwardly from first side 104. In some embodiments, channel 120 terminates at a rear wall 122 that extends between the side walls 116, 118 as best seen in FIG. 4. Rear wall 122 may form channel 120 with side walls 116, 118 and upper wall 124. Channel 120 may be sized and configured to receive an artificial joint or articular surface 200 (FIG. 10), which may be artificial joint surface 22 disclosed in the '362 Patent and/or poly implant/insert 1300 disclosed in the '904 Patent for example. As best seen in FIG. 4, the upper wall 124 may include a recessed area 126 that is sized and configured to receive a locking tab provided on an upper surface of the artificial joint surface that may be received within channel 120.

Figure 2:
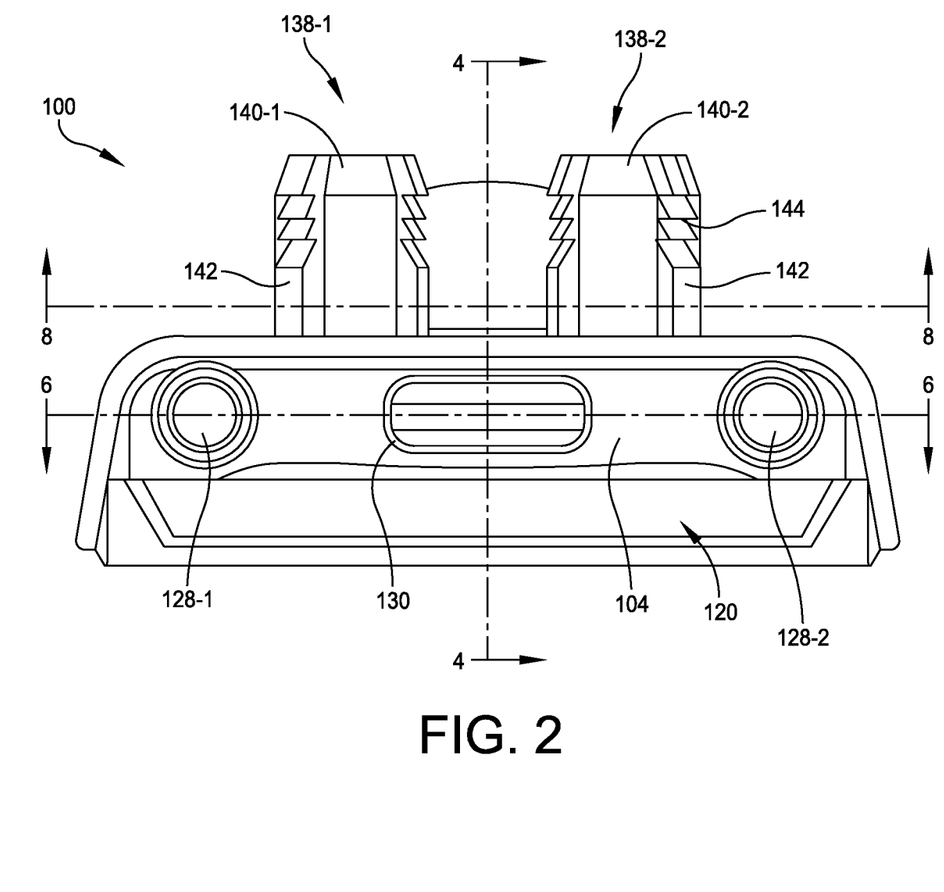
FIG. 2 is a front side view of the prosthesis illustrated in FIG. 1 in accordance with some embodiments.
Figure 6:
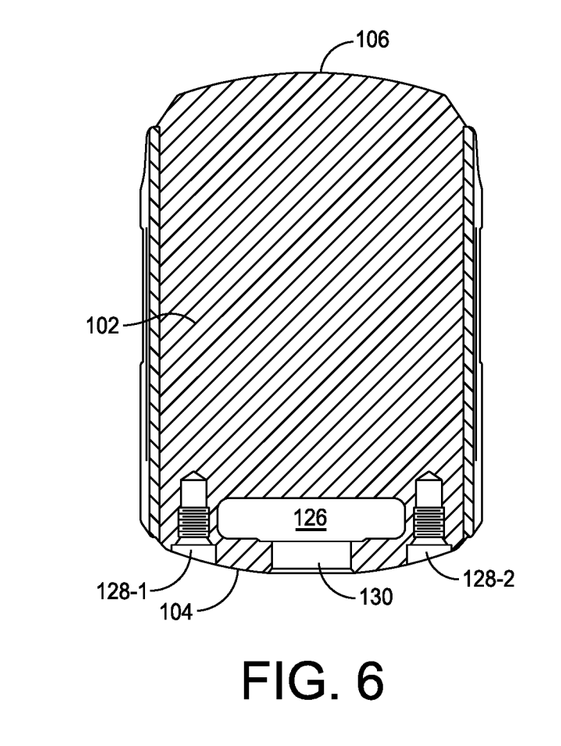
FIG. 6 is a sectional view of the prosthesis illustrated in FIG. 1 taken along line 6-6 in FIG. 2 in accordance with some embodiments.
Figure 7:
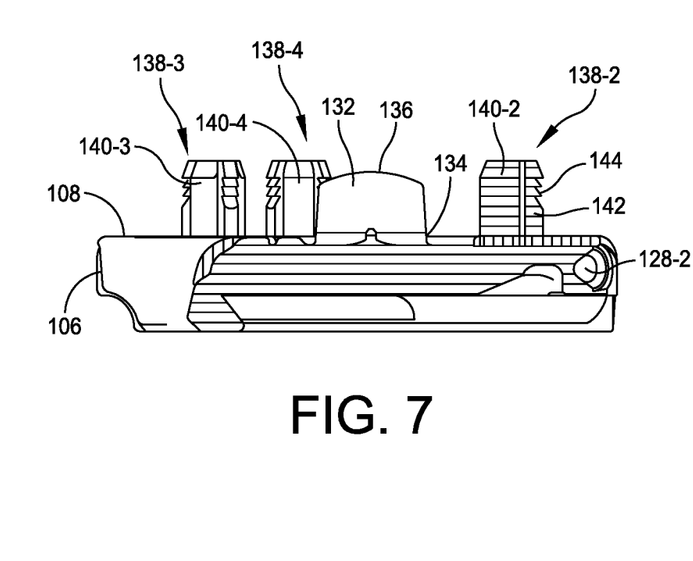
FIG. 7 is a sectional view of the prosthesis illustrated in FIG. 1 taken along line 7-7 in FIG. 3 in accordance with some embodiments.
Figure 8:
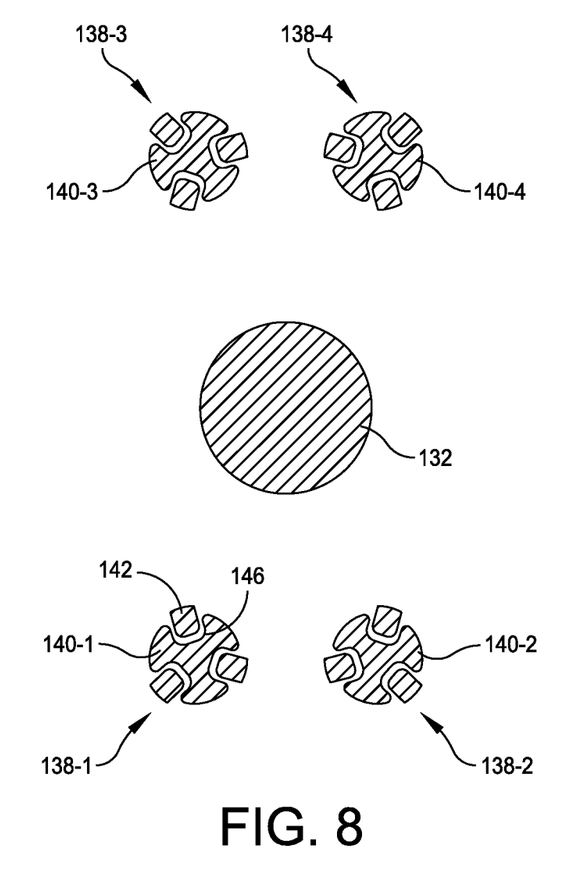
FIG. 8 is a sectional view of the prosthesis illustrated in FIG. 1 taken along line 8-8 in FIG. 2 in accordance with some embodiments.
Figure 10:
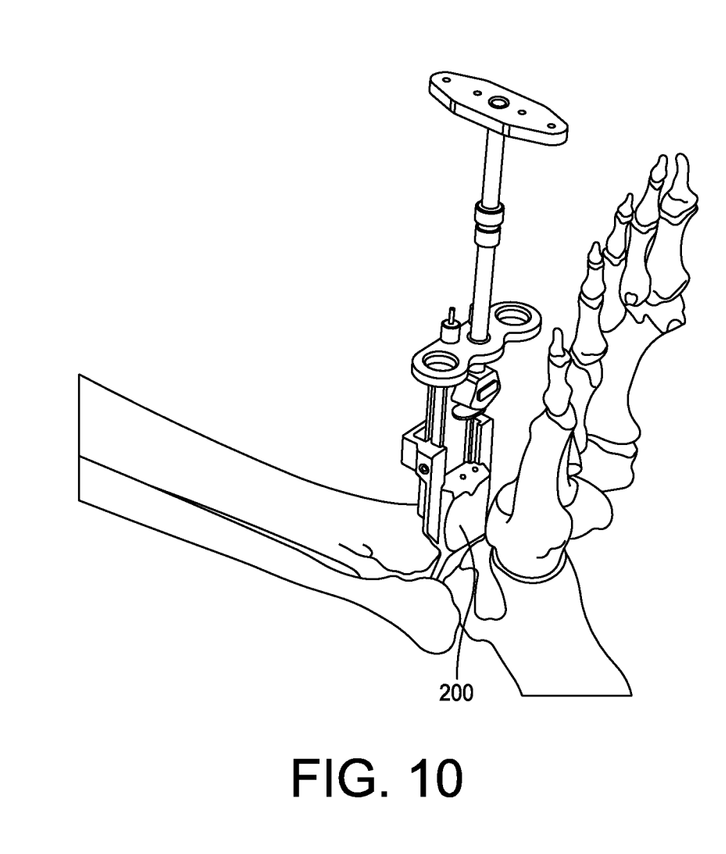
FIG. 10 illustrates the prosthesis illustrated in FIG. 1 receiving an artificial joint surface using an insertion tool in accordance with some embodiments.

Referring now to FIGS. 1, 2, and 4, side 104 may define one or more holes 128-1, 128-2 (collectively, "holes 128"). Holes 128 may be blind holes that are spaced apart from one another along the front side 104. In some embodiments, holes 128 are blind holes sized and configured to be engaged by an attachment screw, such as attachment screws 3500 disclosed in the '904 Patent and as illustrated in FIG. 10. For example, holes 128 may be at least partially threaded along their length such that the threads of holes 128 may be engaged by corresponding threads on an attachment screw as best seen in FIG. 6. One of ordinary skill in the art will understand that holes 128 may take other configurations and be located at different locations alongside 104. A slot 130 may be defined by the front side 104 as also shown in FIGS. 1, 2, and 4. In some embodiments, slot 130 extends through side 104 and is in communication with channel 120 via recessed area 126. In some embodiments, slot 130 provides access to recessed area 126 to facilitate removal of an artificial joint surface received within channel 120 as a tool may be inserted into slot 130 to disengage a detent provided by the artificial joint surface that is received within recessed area 126. In some embodiments, the slot 130 is configured to engage a poly insertion tool, such as poly insertion tool 3100 disclosed in U.S. Pat. No. 10,136,904, which was incorporated by reference above.

Figure 9:
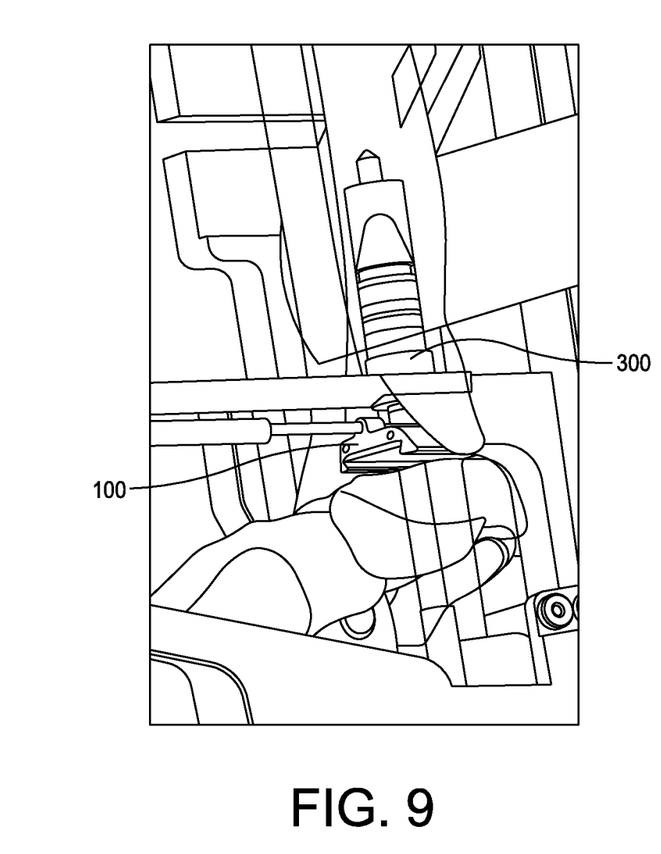
FIG. 9 illustrates the prosthesis illustrated in FIG. 1 being coupled to a prosthesis stem in accordance with some embodiments.

A stem 132 may extend upwardly from side 108. In some embodiments, stem 132 tapers along its length such that stem 132 is wider at its base 134 (e.g., adjacent to surface 110) and narrower at or near its apex or upper end 136. One of ordinary skill in the art will understand that stem 132 may be cylindrically shaped such that stem 134 does not taper along its length. In some embodiments, stem 134 is to engage a bone, such as a tibia. For example, stem 134 may include a coating or a porous structure to promote bony ingrowth as will be understood by one of ordinary skill in the art. However, in some embodiments, stem 134 is configured to engage another prosthesis component, such as a stem component of a multi-component prosthesis stem. For example, stem 134 may engage another component of prosthesis stem 300 (e.g., a single or multi-component prosthesis stem) via Morse taper coupling as illustrated in FIG. 9. Other mechanisms through which prosthesis 100 may be coupled to other prosthesis components are described in commonly assigned U.S. Provisional Patent Application No. 63/169,306, filed Apr. 1, 2021, and entitled "Coupling Systems and Methods," the entirety of which is incorporated by reference herein.

One or more fixation elements 138-1, 138-2, 138-3, 138-4 (collectively, "fixation elements 138"), which may take the form of pegs 140-1, 140-2, 140-3, 140-4 (collectively, "pegs 140"), may also extend upwardly from side 108. In some embodiments, pegs 140 may extend upwardly from side 108 at an oblique angle with respect to a planar surface defined by side 108. In such embodiments, stem 134 may be omitted or also extend upwardly at an oblique angle. Although four fixation elements 138 are shown, it should be understood that fewer (e.g., one, two, or three) or more (e.g., five or more) fixation elements 138 may be provided. In some embodiments, fixation elements 138 are arranged such that stem 134 is positioned at an approximate or relative center of fixation elements 138, although one of ordinary skill in the art will understood that the relative position of stem 134 and fixation elements 138 may vary.

Figure 3:
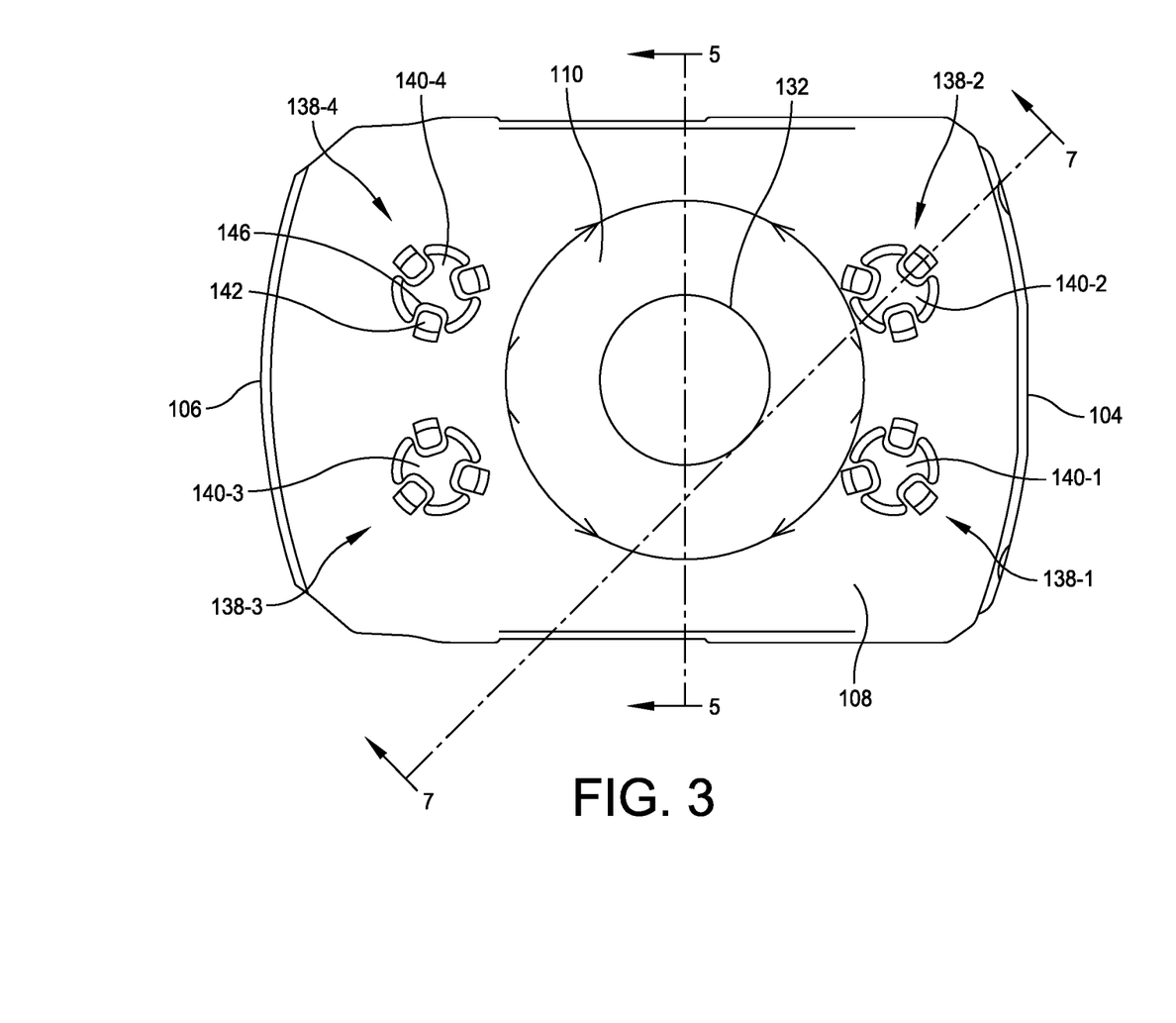
FIG. 3 is a top side view of the prosthesis illustrated in FIG. 1 in accordance with some embodiments.

As best seen in FIGS. 1 and 3, fixation elements 138 may include one or more prongs 142-1, 142-2, 142-3 (collectively, "prongs 142"). Although three prongs 142 are illustrated, one of ordinary skill in the art will understand that fewer or more prongs 142 may be provided on a per-peg basis. One or more prongs 142 may be formed as part of a peg 140, or one or more prongs 142 may be a separate and independent structure with respect to pegs 140. For example, when formed as separate and independent structures, pegs 140 may extend from upper surface 110 of side 108 without physically contacting a prong 142, which also extends from upper surface 110 of side 108.

In some embodiments, prongs 142 may be positioned within cutouts 146 defined by pegs 140 as best seen in FIG. 3. Cutouts 146 provide clearance for prongs 142 so that the prongs 142 may be flexed toward pegs 140. Prongs 142 may include one or more frictional elements 144 as best seen in FIGS. 1 and 2. Frictional elements 144 may take the form of serrations, teeth, barbs, or other structures designed and adapted to dig into surrounding bone as will be understood by one of ordinary skill in the art. In some embodiments, pegs 140 and/or prongs 142 may include a taper to facilitate insertion of the pegs and/or prongs 142 into bone. For example, pegs 140 and/or prongs 142 may taper along their entire lengths such that they are narrower at their respective tops than they are at their respective bases, or pegs 140 and/or prongs 142 may taper only over a portion of their lengths, such as by including a taper adjacent to an upper end.

Body 102 may be formed from one or more materials and/or one or more manufacturing processes. In some embodiments, a first portion 102-1 of body 102 (e.g., the darker shaded portion in FIG. 1) may be formed from a first material using a first manufacturing process and a second portion 10202 (e.g., the lighter shaded portion in FIG. 1) may be formed from a second material using a second manufacturing process. For example, portion 102-1 may be formed from a biologically compatible material (e.g., titanium, cobalt) and be manufactured using one or more of a forging, die-casting, or 3D printing process, and portion 102-2 may be formed from a different biologically compatible material, such as BIOFOAM®, available from Wright Medical Technology, Inc. In some embodiments, portion 102-2 is formed by plasma spray deposition. One of ordinary skill in the art will understand that the first and/or second portions 102-1, 102-2 of body 102 may be impregnated and/or coated with one or more growth factors to enhance bone ingrowth and fixation.

In use, the prosthesis 100 may be installed or implanted by first preparing a bone or joint surface for receiving the prosthesis. For example, in embodiments in which the prosthesis is to be implanted in a distal tibia, the distal tibia may be resected. The resections may be performed using various tooling and techniques, such as those disclosed in the '362 Patent and/or the '904 Patent. In addition to resecting the distal tibia to create a suitable implantation site, an intramedullary canal for receiving the stem 132 and one or more holes for receiving pegs 138 may be drilled, reamed, or otherwise formed in the distal tibia.

In some embodiments, a prosthesis may include a body extending along a length from a first side to a second side and may include a third side disposed between the first side and the second side. The body may include a pair of spaced apart rails between which a channel may be defined. A stem and a first fixation element may extend upwardly from the third side.

In some embodiments, the first fixation element may include a peg.

In some embodiments, the first fixation element may include at least one prong.

In some embodiments, the at least one prong may be disposed adjacent to the first peg.

In some embodiments, the at least one prong may include a frictional element disposed along a length of the at least one prong.

In some embodiments, the frictional element may include at least one of a barb or a tooth.

In some embodiments, the first fixation element may include a plurality of prongs disposed adjacent to the peg.

In some embodiments, the plurality of prongs may be configured to flex.

In some embodiments, each of the plurality of prongs may include a first element disposed on a surface thereof.

In some embodiments, a second fixation element may extend upwardly from the third side.

In some embodiments, the first fixation element may include a first peg, and the second fixation element may include a second peg.

In some embodiments, the first fixation element may include at least one first prong associated with the first peg.

In some embodiments, the first fixation element may include at least one first prong associated with the first peg. The second fixation element may include at least one second prong associated with the second peg.

In some embodiments, the body may include first portion formed from a first material and a second portion formed from a second material.

In some embodiments, the first material is different from the second material.

In some embodiments, the first portion may be formed using a first manufacturing process, and the second portion may be formed using a second manufacturing process. In some embodiments, the first manufacturing process is different from the second manufacturing process.

In some embodiments, the stem may be configured to be received within a hole defined by another prosthesis component.

In some embodiments, the stem may be configured to engage bone directly.

In some embodiments, a system may include a first prosthesis. The first prosthesis may include a body extending along a length from a first side to a second and may include a third side disposed between the first side and the second side. The body may include a pair of spaced apart rails between which a channel may be defined. A stem and a first fixation element may extend upwardly from the third side.

In some embodiments, a second prosthesis may be sized and configured to be received within the channel defined by the body first prosthesis.

In some embodiments, the second prosthesis may include an artificial joint surface.

In some embodiments, the first fixation element may include a peg.

In some embodiments, the first fixation element may include at least one prong.

In some embodiments, the at least one prong may be disposed adjacent to the first peg.

In some embodiments, the at least one prong may include a frictional element disposed along a length of the at least one prong.

In some embodiments, the frictional element may include at least one of a barb or a tooth.

In some embodiments, the first fixation element may include a plurality of prongs disposed adjacent to the peg.

In some embodiments, the plurality of prongs may be configured to flex.

In some embodiments, each of the plurality of prongs may include a first element disposed on a surface thereof.

In some embodiments, a second fixation element may extend upwardly from the third side.

In some embodiments, the first fixation element may include a first peg, and the second fixation element may include a second peg.

In some embodiments, the first fixation element may include at least one first prong associated with the first peg.

In some embodiments, the first fixation element may include at least one first prong associated with the first peg. The second fixation element may include at least one second prong associated with the second peg.

In some embodiments, the body of the first prosthesis may include first portion formed from a first material and a second portion formed from a second material.

In some embodiments, the first material may be different from the second material.

In some embodiments, the first portion may be formed using a first manufacturing process, and the second portion may be formed using a second manufacturing process. In some embodiments, the first manufacturing process is different from the second manufacturing process. In some embodiments, the first manufacturing process and the second manufacturing process are the same manufacturing process.

In some embodiments, the stem may be configured to be received within a hole defined by another prosthesis component.

In some embodiments, the stem may be configured to engage bone directly.

In some embodiments, a second fixation element may extend upwardly from the third side of the first prosthesis. The first fixation element may be disposed adjacent to the first side, the second fixation element may be disposed adjacent to the second side, and the stem may be disposed between the first fixation element and the second fixation element.

In some embodiments, a third fixation element may extend upwardly from the third side and may be disposed adjacent to the first fixation element. A fourth fixation element may extend upwardly from the third side and may be disposed adjacent to the second fixation element.

In some embodiments, a method may include coupling a first prosthesis to a bone. The first prosthesis may include a body extending along a length from a first side to a second and may include a third side disposed between the first side and the second side. The body may include a pair of spaced apart rails between which a channel may be defined. A stem and a first fixation element may extend upwardly from the third side.

In some embodiments, coupling the first prosthesis to the bone may include inserting the first fixation element into a hole formed in the bone.

In some embodiments, a method includes forming the hole in the bone.

In some embodiments, coupling the first prosthesis to the bone may include inserting the stem into an intramedullary canal formed in the bone.

In some embodiments, a method may include forming the intramedullary canal in the bone.

In some embodiments, coupling the first prosthesis to the bone may include inserting the stem into a corresponding recess defined by a second prosthesis.

In some embodiments, a method may include coupling the second prosthesis to the bone prior to inserting the stem into the corresponding recess defined by the second prosthesis.

In some embodiments, the bone is a tibia.

Although the prostheses, systems, and methods have been described in terms of exemplary embodiments, they are not limited thereto. Rather, the appended claims should be construed broadly, to include other variants and embodiments of the prostheses, systems, and methods, which may be made by those skilled in the art without departing from the scope and range of equivalents of the prostheses, systems, and methods.

What is claimed is:

1. A system, comprising:
   a first prosthesis, the first prosthesis including a body extending along a length from a first side to a second side and including a third side disposed between the first side and the second side, the body including a pair of spaced apart rails between which a channel is defined,
   wherein a stem projects from a center portion of the third side and a first fixation element extends upwardly from the third side in spaced relation to the stem, wherein the first fixation element includes a peg defining a longitudinal cutout in an outer surface that extends the length of the peg, the cutout sized to accept a portion of a flexible prong that is integral with and projecting outwardly from the third side laterally adjacent to the cutout, the flexible prong being arranged to flex toward the peg so as to enter the cutout laterally when frictionally engaging a bone surface.

2. The system of claim 1, further comprising a second prosthesis sized and configured to be received within the channel defined by the body of the first prosthesis.

3. The system of claim 2, wherein the second prosthesis includes an artificial joint surface.

4. The system of claim 3, wherein the flexible prong includes a frictional element disposed along a length of the flexible prong.

5. The system of claim 4, wherein the frictional element includes at least one of a barb or a tooth.

6. The system of claim 1, wherein the first fixation element includes a plurality of flexible prongs each disposed adjacent to a longitudinal cutout in an outer surface that extends along the length of the peg to the third side and circumferentially spaced apart from one another.

7. The system of claim 6, wherein each flexible prong of the plurality of flexible prongs is configured to flex toward the peg so as to enter the cutout laterally.

8. The system of claim 6, wherein each flexible prong of the plurality of flexible prongs includes a first frictional element disposed on a surface thereof.

9. The system of claim 1, further comprising a second fixation element extending upwardly from the third side, the second fixation element having a peg defining longitudinal cutout in an outer surface that extends along the length of the peg, the cutout is sized to accept a portion of a flexible prong that is integral with and projecting outwardly from the third side laterally adjacent to the cutout, the flexible prong being arranged to flex toward the peg so as to enter the cutout laterally when frictionally engaging a bone surface.

10. The system of claim 9, wherein the first fixation element includes a first peg with a first plurality of flexible prongs each disposed adjacent a longitudinal cutout in an outer surface that extends along the length of the peg and circumferentially spaced apart from one another and the second fixation element includes a second peg with a second plurality of flexible prongs each disposed adjacent to a longitudinal cutout in an outer surface that extends along the length of the peg and circumferentially spaced apart from one another.

11. The system of claim 1, wherein the body of the first prosthesis includes first portion formed from a first material and a second portion formed from a second material.

12. The system of claim 9, further comprising:
   a third fixation element extending upwardly from the third side includes a third peg with a third plurality of flexible prongs each disposed adjacent a longitudinal cutout in an outer surface that extends along the length of the peg and circumferentially spaced apart from one another and disposed adjacent to the first fixation element, and
   a fourth fixation element extending upwardly from the third side includes a fourth peg with a fourth plurality of flexible prongs each disposed adjacent a longitudinal cutout in an outer surface that extends along the length of the peg and circumferentially spaced apart from one another and disposed adjacent to the second fixation element.

13. A method, comprising:
   coupling a first prosthesis to a bone, wherein the first prosthesis includes a body extending along a length from a first side to a second side and including a third side disposed between the first side and the second side, the body including a pair of spaced apart rails between which a channel is defined, wherein a stem projects from a center portion of the third side and a first fixation element extends upwardly from the third side in spaced relation to the stem, wherein the first fixation element includes a peg defining a longitudinal cutout in an outer surface that extends along the length of the peg, the cutout sized to accept a portion of a flexible prong that is integral with and projecting outwardly from the third side laterally adjacent to the cutout, the flexible prong being arranged to flex toward the peg so as to enter the cutout laterally when frictionally engaging a bone surface.

14. The method of claim 13, wherein coupling the first prosthesis to the bone includes inserting the first fixation element into a hole formed in the bone such that a prong engages the bone and flexes inwardly into the cutout.

15. The method of claim 14, wherein coupling the first prosthesis to the bone includes inserting the stem into an intramedullary canal formed in the bone.

16. The method of claim 14, wherein coupling the first prosthesis to the bone includes inserting the stem into a corresponding recess defined by a second prosthesis.

17. The method of claim 16, further comprising coupling the second prosthesis to the bone prior to inserting the stem into the corresponding recess defined by the second prosthesis.

* * * * *